United States Patent
Martinez et al.

(12)

(10) Patent No.: US 6,288,240 B1
(45) Date of Patent: *Sep. 11, 2001

(54) PREPARATION OF 2-HYDROXY-5-OXOPROLINE AND ANALOGS THEREOF

(75) Inventors: Rodolfo A. Martinez, Santa Fe; Pat J. Unkefer, Los Alamos, both of NM (US)

(73) Assignee: The Regents of the University of California, Los Alamos, NM (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/584,621

(22) Filed: May 31, 2000

(51) Int. Cl.$^7$ .................................................. C07D 207/28
(52) U.S. Cl. ............................................... 548/534
(58) Field of Search ........................................... 548/534

(56) References Cited

PUBLICATIONS

Cooper et al., J. Biol. Chem., 248, 1973, 8499–8505.*
U.S. Patent and Trademark Office Serial No. 09/493,039 "Use of Prolines For Improving Growth And Other Properties Of Plants And Algae" by Pat J. Unkefer, Thomas J. Knight, and Rodolfo A. Martinez, filed on Jan. 27, 2000.
Arthur J.L. Cooper and Alton Meister, "The Glutamine Tranaminase–ω–Amidase Pathway" CRC Critical Reviews in Biochemistry, pp. 281–303, Jan. 1977.
Masayuki Ohmori et al., "Occurrence Of Glutamine–2–Oxoacid Transaminase Activity In The Blue–Green Alga *ANABAENA CYLINDRICA*", J. Gen Appl. Microbiol. 31, 171 (1985).
Angel Garcia–Raso, "Oxidation of α–Amino Acids and α–Hydroxy Acids By Fremy's Salt. A Model For Oxidases?", J. Org. Chem. 51, 4285 (1986).
W. Moser and R.A. Howie, "Nitrosodisulphonates, Part I. Fremy's Salt (Potassium Nitrosodisulphonate)", J. Chem. Soc. A 3039 (1968).

* cited by examiner

Primary Examiner—Fiona T. Powers
(74) Attorney, Agent, or Firm—Samuel M. Freund

(57) ABSTRACT

The compound 2-hydroxy-5-oxoproline and analogs thereof may be used to produce an increase in carbon dioxide fixation, growth, dry weight, nutritional value (proteins and amino acids), nodulation and nitrogen fixation and photosynthetically derived chemical energy when applied to plants through their roots and/or through their foliar portions. The present invention includes an essentially quantitative chemical synthesis for this compound which is performed in a single step reaction of Fremy's Salt (potassium nitrosodisulphonate) with either glutamine or 2-pyrrolidone-5-carboxylic acid. Fremy's salt (potassium nitrosodisulphonate) is available commercially, or can be readily synthesized.

11 Claims, No Drawings

US 6,288,240 B1

PREPARATION OF 2-HYDROXY-5-OXOPROLINE AND ANALOGS THEREOF

STATEMENT REGARDING FEDERAL RIGHTS

This invention was made with government support under Contract No. W-7405-ENG-36 awarded by the U.S. Department of Energy to The Regents of The University of California. The government has certain rights in the invention.

FIELD OF THE INVENTION

The present invention relates generally to the preparation of certain prolines and, more particularly, to the preparation of the sodium salt of 2-hydroxy-5-oxoproline.

BACKGROUND OF THE INVENTION

The metabolite 2-hydroxy-5-oxoproline (2-oxoglutaramate) was discovered several decades ago in animal livers and kidneys and investigated in these tissues. A limited understanding of its function in animals was developed from these studies; in cells this material appears to be made by the physiologically irreversible transamination of glutamine. The compound appears to play a role in the regulation of tissue glutamine levels and in ammoniagenesis; that is, the amide nitrogen in glutamine is a major source of urinary ammonia. See, e.g., "The Glutamine Tranaminase-ω-Amidase Pathway" by Arthur J. L. Cooper and Alton Meister, CRC Critical Reviews in Biochemistry, pages 281–303, January 1977, and "Occurrence Of Glutamine-2-Oxoacid Transaminase Activity In The Blue-Green Alga *ANABAENA CYLINDRICA*" by Masayuki Ohmori et al., J. Gen Appl. Microbiol. 31, 171 (1985).

More recently, 2-hydroxy-5-oxoproline has been found to have significant effect on plant growth. See, e.g., "Use Of Prolines For Improving Growth And Other Properties Of Plants And Algae" by Pat J. Unkefer, Thomas J. Knight, and Rodolfo A. Martinez, U.S. Patent and Trademark Office Ser. No. 09/493,039, filed on Jan. 27, 2000, where the inventors describe the use of the chemical class of compounds known as prolines for improving plant properties and performance.

In the past, 2-hydroxy-5-oxoproline has been synthesized using enzymatic procedures which are slow and difficult to control. See, e.g., A. L. Cooper and Alton Meister, supra.

The reaction of Fremy's Salt with glutamic acid to yield (21%) an α-ketoacid of glutamic acid is described in "Oxidation of α-Amino Acids and α-Hydroxy Acids By Fremy's Salt. A Model For Oxidases?" by Angel Garcia-Raso, J. Org. Chem. 51, 4285 (1986). More particularly, α-glutamic acid was used as the starting material and the following reactions were observed:

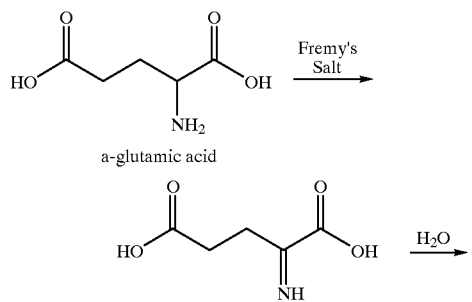

However, the final product does not cyclize.

Accordingly, it is an object of the present invention to provide a method for synthesizing 2-hydroxy-5-oxoproline and analogs thereof in an inexpensive, bulk process.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for preparing 2-hydroxy-5-oxoproline hereof is performed in a single step reaction of Fremy's Salt (potassium nitrosodisulphonate) with either glutamine or 2-pyrrolidone-5-carboxylic acid. Fremy's salt (potassium nitrosodisulphonate) is available commercially, or can be readily synthesized.

Benefits and advantages of the present invention include an inexpensive, essentially quantitative, readily performed, single-step synthetic procedure for preparing large quantities of 2-hydroxy-5-oxoproline.

DETAILED DESCRIPTION

The present invention includes an efficient, inexpensive procedure for preparing 2-hydroxy-5-oxoproline and analogs thereof. The compound is synthesized in a single step by the action of Fremy's salt (potassium nitrosodisulphonate) on either glutamine or on 2-pyrrolidone-5-carboxylic acid. Fremy's salt (potassium nitrosodisulphonate) is available commercially, or can be synthesized in accordance with the procedure described in "Nitrosodisulphonates, Part I. Fremy's Salt (Potassium Nitrosodisulphonate)" by W. Moser and R. A. Howie, J. Chem. Soc. A 3039 (1968).

Reference will now be made in detail to the present preferred embodiments of the invention.

I. Synthesis of 2-hydroxy-5-oxoproline Using 2-pyrrolidone-5-carboxylic Acid:

1) A buffer solution containing 1.3 M Sodium bicarbonate (NaHCO₃) and having a pH of approximately 9.5 adjusted to this value by addition of 10 M Sodium Hydroxide (NaOH) is first prepared;
2) 30.0 g of 2-pyrrolidone-5-carboxylic acid is dissolved in 500 ml of the Sodium bicarbonate buffer solution with moderate stirring using a magnetic stir plate, in a 2 L, two- or three-neck, round-bottom flask;
3) The Fremy's Salt is then added to the solution and an additional 300 ml of the sodium bicarbonate buffer added. The pH of the solution is maintained at between 9.0–9.5. The reaction is stirred at room temperature for 30–48 h or until the solution becomes colorless, at which point another equivalent of Fremy's Salt is added and the reaction allowed to continue for another 30–48 h or until the solution becomes colorless. NMR analysis is performed on the solution to determine whether the reaction is complete; if not, additional Fremy's Salt can be added to drive the reaction to completion. The following reactions illustrate the above-described synthesis:

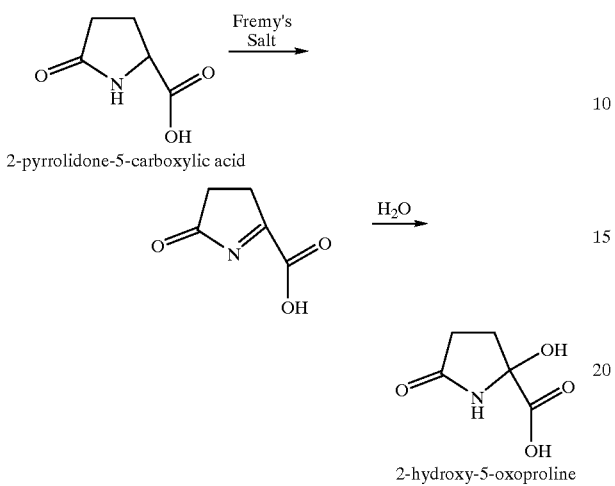

4) After completion of the reaction, the pH is adjusted to a value of 4.5 using the proton form of Dowex 50×8 resin, the resin is removed by filtration, the supernatant is dried, and the 2-hydroxy-5-oxoproline was is isolated by extraction with dimethylsulfoxide. The synthesis was found to produce approximately 30 g of 2-hydroxy-5-oxoproline. The yield of 2-hydroxy-5-oxoproline is quantitative.

II. Synthesis of 2-hydroxy-5-oxoiproline Using Glutamine:

The synthesis of 2-hydroxy-5-oxoproline from glutamine as a starting material is similar to that using 2-pyrrolidone-5-carboxylic acid. The relevant reactions are as follows:

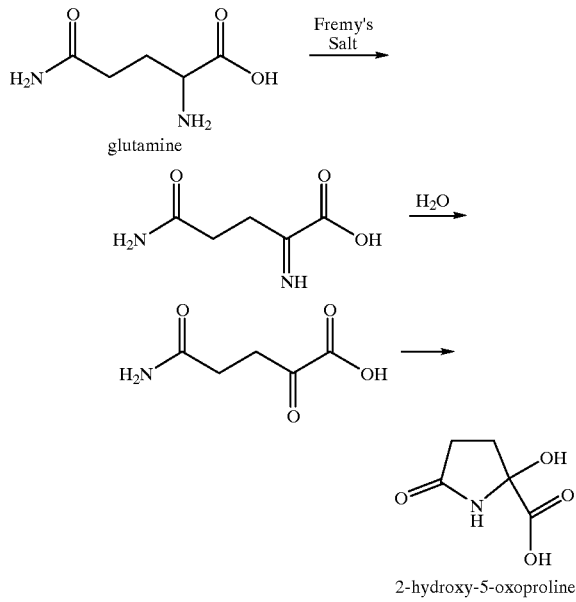

Fremy's Salt (1.5 mmole) was added to a solution of 0.5 mmole of glutamine in 10 ml of sodium bicarbonate buffer (pH 9.5). The reaction was stirred at room temperature and monitored daily by 13C-NMR for the disappearance of the starting material and the appearance of the desired product. The glutamine was completely converted to the desired product in 4 days. The reaction mixture was evaporated to dryness and the 2-hydroxy-5-oxoproline was isolated by extraction with dimethylsulfoxide. The yield for this reaction is quantitative.

The foregoing description of the invention has been presented for purposes of illustration and description and is not intended to be exhaustive or to limit the invention to the precise form disclosed, and obviously many modifications and variations are possible in light of the above teaching. For example, the present synthesis is expected to be effective for the following side groups in the 2-pyrrolidone-5-carboxylic acid and glutamine starting materials, respectively.

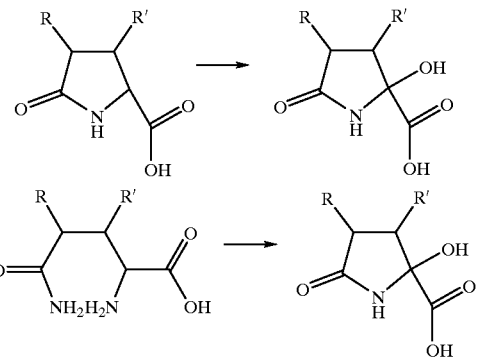

where R and R' include alkyl and aromatic groups.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing 2-hydroxy-5-oxoproline which comprises the steps of:
   (a) dissolving 2-pyrrolidone-5-carboxylic acid in a pH buffer solution; and
   (b) reacting Fremy's Salt with the solution of 2-pyrrolidone-5-carboxylic acid in a pH buffer solution such that 2-hydroxy-5-oxoproline is formed.

2. The method for preparing 2-hydroxy-5-oxoproline as described in claim 1, wherein said buffer solution includes sodium bicarbonate.

3. The method for preparing 2-hydroxy-5-oxoproline as described in claim 1, wherein the pH of said solution containing Fremy's Salt and 2-pyrrolidone-5-carboxylic acid in a pH buffer solution is maintained at a value between 9.0 and 9.5.

4. The method for preparing 2-hydroxy-5-oxoproline as described in claim 1, further including the steps of adjusting the pH of said solution containing the reaction products of Fremy's Salt and 2-pyrrolidone-5-carboxylic acid in a pH buffer solution to a value of 4.5, removing the water from the resulting solution and extracting the 2-hydroxy-5-oxoproline using a solvent therefor.

5. The method for preparing 2-hydroxy-5-oxoproline as described in claim 4, wherein said solvent for 2-hydroxy-5-oxoproline includes dimethylsulfoxide.

6. The method for preparing 2-hydroxy-5-oxoproline as described in claim 1, wherein an excess of Fremy's Salt over the stoichiometric quantity thereof required is added to said solution 2-pyrrolidone-5-carboxylic acid in a pH buffer solution.

7. A method for preparing 2-hydroxy-5-oxoproline which comprises the steps of:

(a) dissolving glutamine in a pH buffer solution; and (b) reacting Fremy's Salt with the solution of glutamine in a pH buffer solution such that 2-hydroxy-5-oxoproline is formed.

8. The method for preparing 2-hydroxy-5-oxoproline as described in claim 1, wherein said buffer solution includes sodium bicarbonate.

9. The method for preparing 2-hydroxy-5-oxoproline as described in claim 1, wherein the pH of said solution containing Fremy's Salt and glutamine in a pH buffer solution is maintained at a value between 9.0 and 9.5.

10. The method for preparing 2-hydroxy-5-oxoproline as described in claim 1, further including the steps of adjusting the pH of the solution containing the reaction products of Fremy's Salt and 2-pyrrolidone-5-carboxylic acid in a pH buffer solution to a value of 4.5, removing the water from the resulting solution and extracting the 2-hydroxy-5-oxoproline using a solvent therefor.

11. The method for preparing 2-hydroxy-5-oxoproline as described in claim 5, wherein said solvent for 2-hydroxy-5-oxoproline includes dimethylsulfoxide.

* * * * *